United States Patent
Nagasaka et al.

(10) Patent No.: US 9,521,958 B2
(45) Date of Patent: Dec. 20, 2016

(54) GAS CELL AND COATING METHOD OF GAS CELL

(71) Applicant: Seiko Epson Corporation, Tokyo (JP)

(72) Inventors: Kimio Nagasaka, Hokuto (JP); Shinobu Yokokawa, Okaya (JP)

(73) Assignee: Seiko Epson Corporation (JP)

( * ) Notice: Subject to any disclaimer, the term of this patent is extended or adjusted under 35 U.S.C. 154(b) by 2 days.

(21) Appl. No.: 13/780,273

(22) Filed: Feb. 28, 2013

(65) Prior Publication Data

US 2013/0230673 A1    Sep. 5, 2013

(30) Foreign Application Priority Data

Mar. 5, 2012  (JP) ................. 2012-047700

(51) Int. Cl.

| | | |
|---|---|---|
| B32B 1/02 | (2006.01) | |
| A61B 5/04 | (2006.01) | |
| G01R 33/032 | (2006.01) | |
| G01R 33/26 | (2006.01) | |
| G01R 33/28 | (2006.01) | |
| B32B 1/08 | (2006.01) | |

(52) U.S. Cl.
CPC ......... *A61B 5/04005* (2013.01); *G01R 33/032* (2013.01); *G01R 33/26* (2013.01); *G01R 33/282* (2013.01); *A61B 5/04007* (2013.01); *A61B 5/04008* (2013.01); *Y10T 428/13* (2015.01)

(58) Field of Classification Search
CPC ............ B32B 1/02; C07F 7/02; Y10T 428/13; A61B 5/04005; A61B 5/04007; A61B 5/04008; G01R 33/032; G01R 33/26; G01R 33/282

USPC ................ 428/34.1, 34.2, 35.7, 35.9, 36.9
See application file for complete search history.

(56) References Cited

U.S. PATENT DOCUMENTS

| | | | |
|---|---|---|---|
| 3,863,144 A * | 1/1975 | Simpson et al. | ............. 324/301 |
| 5,435,839 A | 7/1995 | Ogawa | |
| 5,545,255 A | 8/1996 | Ogawa | |
| 5,645,633 A | 7/1997 | Ogawa | |
| 5,876,806 A | 3/1999 | Ogawa | |
| 6,086,795 A * | 7/2000 | Hatton | ................... C09J 11/06 |
| | | | 252/301.21 |
| 6,383,677 B1 * | 5/2002 | Allen | ......................... 429/454 |

(Continued)

FOREIGN PATENT DOCUMENTS

| | | |
|---|---|---|
| JP | 06-271840 A | 9/1994 |
| JP | 2009-236599 | 10/2009 |

(Continued)

OTHER PUBLICATIONS

M. A. Bouchiat and J. Brossel, "Relaxation of Optically Rb Atoms on Paraffin-Coated Walls", Physical Review, vol. 147, No. 1, pp. 41-54 (1965).

*Primary Examiner* — Marc A Patterson
(74) *Attorney, Agent, or Firm* — Harness, Dickey & Pierce, P.L.C.

(57) ABSTRACT

A gas cell to be filled with alkali metal atoms includes wall surfaces formed using a compound having polar groups or a material containing the compound, a first coating layer as a coating layer that coats the inner walls, formed using first molecules having functional groups to be chemically bonded to the polar groups and non-polar groups, and a second coating layer formed using non-polar second molecules on the first coating layer.

7 Claims, 10 Drawing Sheets

(56) References Cited

U.S. PATENT DOCUMENTS

| | | | |
|---|---|---|---|
| 6,577,802 B1* | 6/2003 | Chien | C03C 25/1065 385/128 |
| 7,038,450 B2* | 5/2006 | Romalis | G01R 33/02 324/301 |
| 7,531,594 B2* | 5/2009 | Lin et al. | 524/487 |
| 7,662,480 B2* | 2/2010 | Resendes et al. | 428/462 |
| 2003/0157391 A1* | 8/2003 | Coleman et al. | 429/34 |
| 2007/0076776 A1* | 4/2007 | Lust et al. | 372/56 |
| 2007/0120563 A1* | 5/2007 | Kawabata et al. | 324/244.1 |
| 2007/0167723 A1* | 7/2007 | Park | B82Y 30/00 600/409 |
| 2008/0069949 A1* | 3/2008 | Glockner et al. | 427/240 |

FOREIGN PATENT DOCUMENTS

| | | | |
|---|---|---|---|
| JP | 2009-236599 A | * | 10/2009 |
| JP | 2010-085134 A | | 4/2010 |

\* cited by examiner

GAS CELL AND COATING METHOD OF GAS CELL

BACKGROUND

1. Technical Field

The present invention relates to a gas cell and a coating method of the gas cell.

2. Related Art

Light pumping magnetic sensors have been used as biomagnetic measurement equipment for detecting a magnetic field generated from a heart of a living body or the like. Patent Document 1 (JP-A-2009-236599) discloses a gas cell, a magnetic sensor using pump light and probe light. In the magnetic sensor, atoms enclosed in the gas cell are excited by the pump light and spin polarization is caused. The polarization plane of the probe light transmitted through the gas cell rotates in response to a magnetic field, and thus, the magnetic field is measured using the rotation angle of the polarization plane of the probe light. Further, as a method of coating inner wall surfaces of the gas cell, for example, Non-patent Document 1 (M. A. Bouchiat and J. Brossel, "Relaxation of Optically Pumped Rb Atoms on Paraffin-Coated Walls", Physical Review Vol. 147, No. 1, pp. 41-54 (1965) discloses an anti-relaxation coated cell using paraffin.

In the technology disclosed in Non-patent Document 1, the number of collisions of atoms with cell inner walls within a time period in which the spin polarization of the atoms disappears is used as an indicator representing anti-relaxation performance of the coating. Its value is about 10,000 and the paraffin coating has a sufficient effect for improvement of magnetic field sensitivity. However, there has been a problem that the anti-relaxation characteristics are deteriorated when the cell is heated to 50° C. or higher.

The paraffin molecule has a structure with a relatively long normal chain, and thus, strong attractive forces act in the entire molecules even when the van der Waals's forces between the atoms are weak. However, the inner wall surfaces of the gas cell (formed principally using borosilicate glass or quartz) are covered by polar groups represented by silanol groups, and thus, it is estimated that, while the attractive forces of the van der Waals's forces or the like acts on the paraffin molecules, they are easily separated by the hydrophobic effect and the adsorbed state is easily changed by heating.

On the other hand, not only the physical adsorption of paraffin but also silane-series materials forming a coating layer by bonding by chemical reaction with the inner walls of the gas cell have been proposed. Specifically, OTS (octadecyltrichlorosilane, $C_{18}H_{37}C_{13}Si$) or the like is used. The material has good temperature characteristics and its heat resistance up to about 150° C. is confirmed. However, the number of collisions until the spin polarization disappears is about 2,100 at most and lower than that of paraffin.

SUMMARY

An advantage of some aspects of the invention is to provide a technology of achieving a balance between anti-relaxation characteristics and heat resistance of inner walls of a gas cell.

An aspect of the invention is directed to a gas cell to be filled with alkali metal atoms, including wall surfaces formed using a compound having polar groups or a material containing the compound, a first coating layer as a coating layer that coats the inner walls and is formed using first molecules having functional groups to be chemically bonded to the polar groups and non-polar groups, and a second coating layer formed using non-polar second molecules on the first coating layer. According to the configuration, the polar groups existing on the inner wall surfaces of the gas cell and the functional groups of the first molecules are chemically bonded, and thereby, exposure of the polar groups on the inner wall surfaces of the gas cell is reduced. Further, the first coating layer is further coated with the non-polar second molecules, and anti-relaxation characteristics are improved. Thereby, a balance between anti-relaxation characteristics and heat resistance of the inner walls of the gas cell may be achieved.

In the gas cell according to the aspect of the invention, the non-polar groups and the second molecules may be organic materials. According to the configuration, the polar groups existing on the inner wall surfaces of the gas cell and the functional groups of the first molecules are chemically bonded, and the exposure of the polar groups on the inner wall surfaces of the gas cell is reduced. Further, the first coating layer is further coated with the organic materials, and the anti-relaxation characteristics are improved. Thereby, the balance between anti-relaxation characteristics and heat resistance of the inner walls of the gas cell may be achieved.

In the gas cell according to the aspect of the invention, the first molecules may be a silane coupling agent. According to the configuration, the polar groups existing on the inner wall surfaces of the gas cell and the functional groups of the silane coupling agent are chemically bonded, and the exposure of the polar groups on the inner wall surfaces of the gas cell is reduced. Further, the first coating layer is further coated with the non-polar second molecules, and the anti-relaxation characteristics are improved. Thereby, a balance between anti-relaxation characteristics and heat resistance of the inner walls of the gas cell may be achieved.

In the gas cell according to the aspect of the invention, the second molecules may be hydrocarbon. According to the configuration, the polar groups existing on the inner wall surfaces of the gas cell and the functional groups of the first molecules are chemically bonded, and the exposure of the polar groups on the inner wall surfaces of the gas cell is reduced. Further, the first coating layer is further coated with the hydrocarbon, and the anti-relaxation characteristics are improved. Thereby, the balance between anti-relaxation characteristics and heat resistance of the inner walls of the gas cell may be achieved.

In the gas cell according to the aspect of the invention, the hydrocarbon may be paraffin. According to the configuration, the polar groups existing on the inner wall surfaces of the gas cell and the functional groups of the first molecules are chemically bonded, and the exposure of the polar groups on the inner wall surfaces of the gas cell is reduced. Further, the first coating layer is further coated with the paraffin, and the anti-relaxation characteristics are improved. Thereby, the balance between anti-relaxation characteristics and heat resistance of the inner walls of the gas cell may be achieved.

Another aspect of the invention is directed to a coating method of coating inner walls of a gas cell to be filled with alkali metal atoms, including forming a coating layer by coating the inner walls formed using a compound having polar groups or a material containing the compound with first molecules having functional groups to be chemically bonded to the polar groups and non-polar groups, and forming a coating layer by coating the coating layer with non-polar second molecules. According to the coating method, the polar groups existing on the inner wall surfaces of the gas cell and the functional groups of the first molecules are chemically bonded, and exposure of the polar groups on the inner wall surfaces of the gas cell is reduced. Further, the first coating layer is further coated with the non-polar second molecule, and the anti-relaxation characteristics are improved. Thereby, the balance between anti-relaxation characteristics and heat resistance of the inner walls of the gas cell may be achieved.

BRIEF DESCRIPTION OF THE DRAWINGS

The invention will be described with reference to the accompanying drawings, wherein like numbers reference like elements.

DESCRIPTION OF EXEMPLARY EMBODIMENTS

1. Configuration

Figure 1:
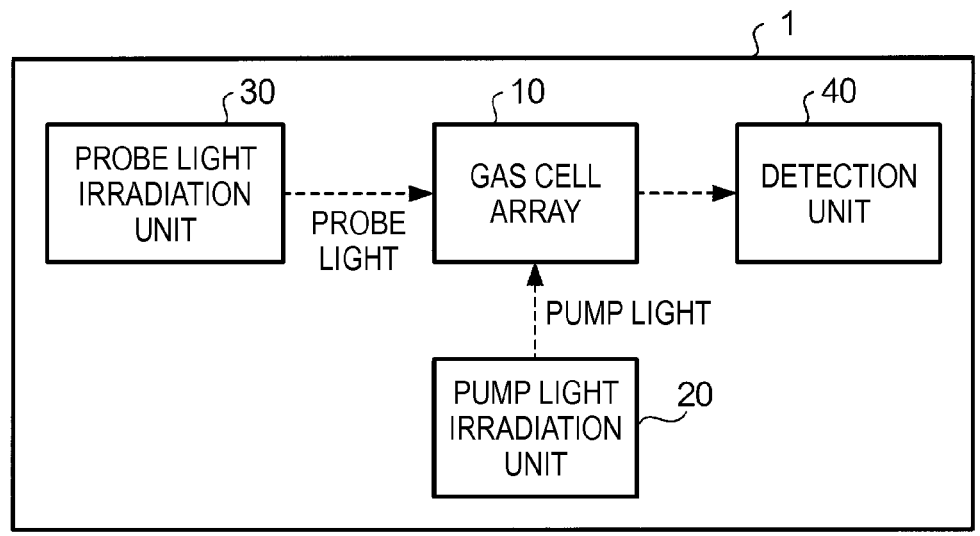
FIG. 1 is a block diagram showing a configuration of magnetic measurement equipment.

FIG. 1 is a block diagram showing a configuration of magnetic measurement equipment 1 according to one embodiment. The magnetic measurement equipment 1 is living body condition measurement equipment that measures a magnetic field generated from a living body such as a magnetic field generated from a heart (magnetocardiography) or a magnetic field generated from a brain (magnetoencephalography) as an indicator of the living body condition. The magnetic measurement equipment 1 includes a gas cell array 10, a pump light irradiation unit 20, a probe light irradiation unit 30, and a detection unit 40. The gas cell array 10 has plural gas cells. Within the gas cell, alkali metal gas (for example, cesium (Cs)) is enclosed. The pump light radiation unit 20 outputs pump light (for example, light having a wavelength of 894 nm corresponding to DI line of cesium) that interacts with alkali metal atoms. The pump light has a circularly-polarized component. When the pump light is radiated, the outermost electrons of the alkali metal atoms are excited and spin polarization is caused. The spin-polarized alkali metal atoms precess according to a magnetic field B generated by an object to be measured. The spin polarization of one alkali metal atom is relaxed over time, and formation and relaxation of spin polarization are repeated simultaneously in parallel and continuously because the pump light is CW (Continuous Wave) light. As a result, if it is regarded as the entire cluster of atoms, steady spin polarization is formed.

The probe light irradiation unit 30 outputs probe light having a linearly-polarized component. Before and after transmission through the gas cell, the polarization surface of the probe light rotates due to the Faraday effect. The rotation angle of the polarization plane is a function of the magnetic field B. The detection unit 40 detects the rotation angle of the probe light. The detection unit 40 includes a photodetector that outputs a signal in response to an amount of incident light, a processor that processes the signal, and a memory that stores data. The processor calculates the magnitude of the magnetic field B using the signal output from the photodetector. The processor writes data representing the calculated result in the memory. In this manner, a user may obtain information of the magnetic field B generated from the object to be measured. Further, non-linear magnetooptics using one beam serving as the pump light and the probe light can be used.

Figure 2:
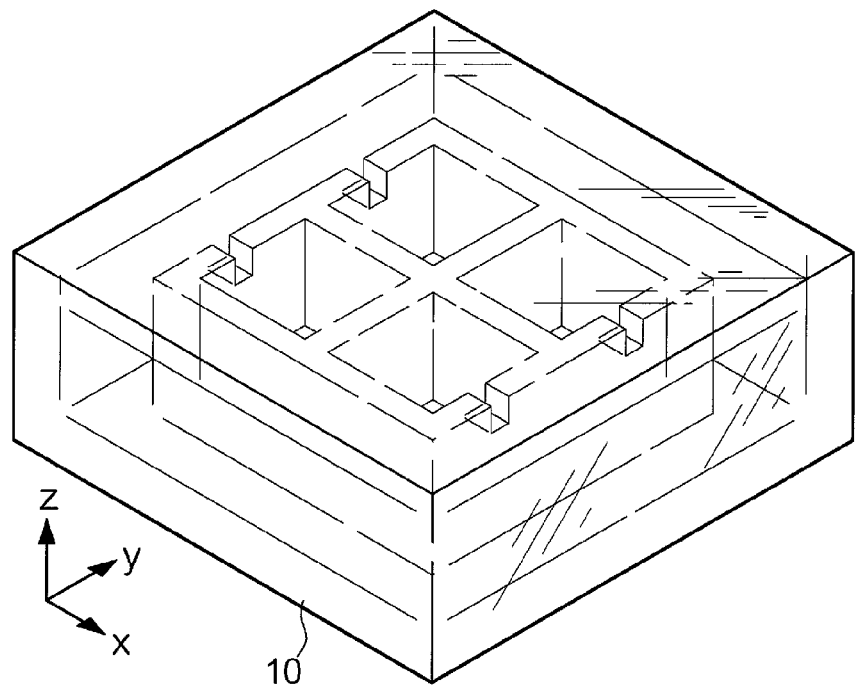
FIG. 2 is an appearance view of a gas cell array.
Figure 3:
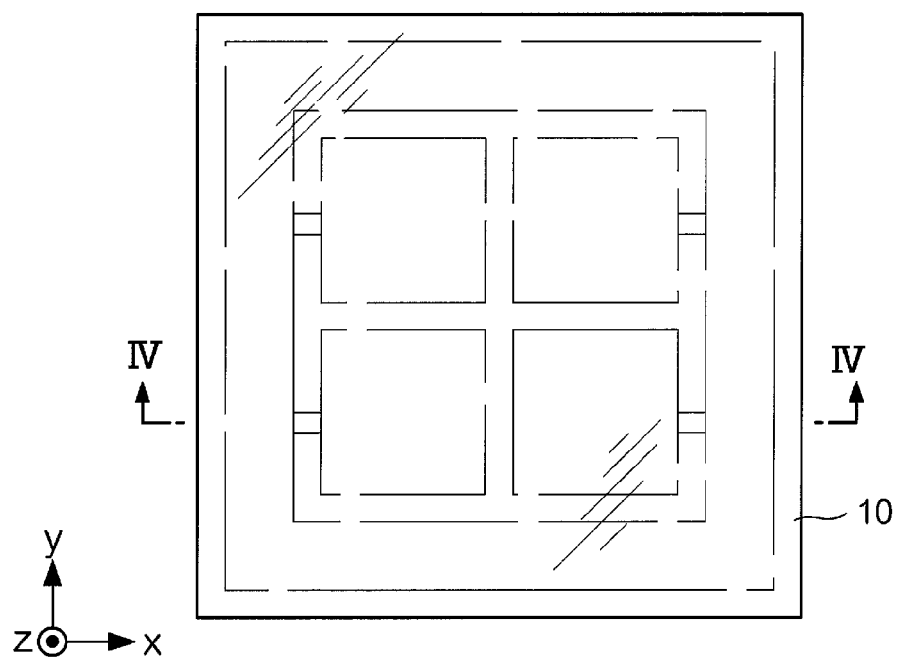
FIG. 3 is a top view of the gas cell array.

FIG. 2 is an appearance view of the gas cell array 10, and FIG. 3 is a top view of the gas cell array 10. Here, "up" refers to the positive z-axis direction in FIG. 2. In this example, the gas cell array 10 has plural (2×2) gas cells two-dimensionally arranged on the xy plane. The gas cell is a rectangular parallelepiped cell (box) in which alkali metal gas is enclosed. The gas cell is formed using a material having light transmissivity such as quartz glass or borosilicate glass. Further, the gas cell array 10 has a dummy cell provided to surround the 2×2 gas cells on the xy plane. The 2×2 gas cells at the center contribute to measurement of the magnetic field, however, the dummy cell does not contribute to the measurement of the magnetic field.

Figure 4:
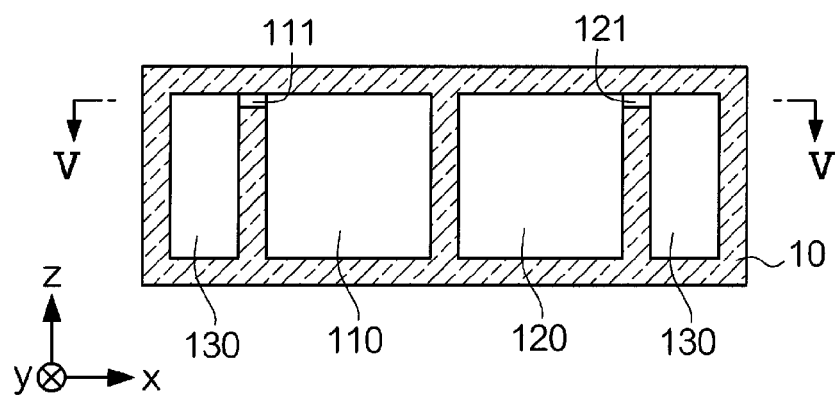
FIG. 4 is a sectional view of the gas cell array along IV-IV.

FIG. 4 is a sectional view of the gas cell array 10 along IV-IV. The section is in parallel to the xz plane. In the section, a gas cell 110, a gas cell 120, and a dummy cell 130 are shown. A through hole 111 is provided between the gas cell 110 and the dummy cell 130. A through hole 121 is provided between the gas cell 120 and the dummy cell 130.

Figure 5:
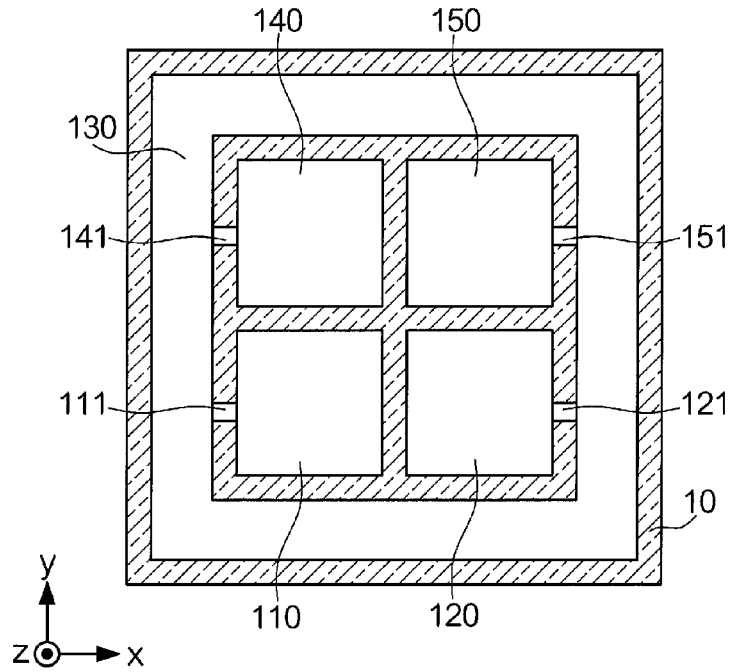
FIG. 5 is a sectional view of the gas cell array along V-V.

FIG. 5 is a sectional view of the gas cell array 10 along V-V. The section is in parallel to the xy plane. In the section, the gas cell 110, the gas cell 120, a gas cell 140, a gas cell 150, and the dummy cell 130 are shown. A through hole 141 is provided between the gas cell 140 and the dummy cell 130. A through hole 151 is provided between the gas cell 150 and the dummy cell 130. The function of the through hole 111, the through hole 121, the through hole 141, and the through hole 151 will be described later.

2. Manufacturing Method

Figure 6:
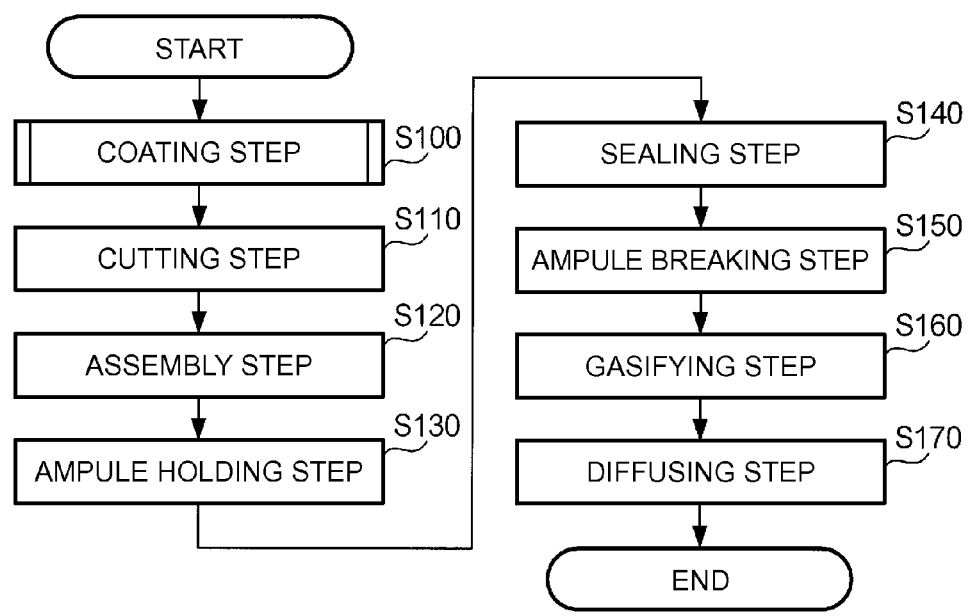
FIG. 6 is a flowchart showing a manufacturing process of the gas cell array.

FIG. 6 is a flowchart showing a manufacturing process of the gas cell array 10. At step S100 (coating step), a coating layer is formed on a glass plate for formation of the gas cell array 10.

Figure 7:
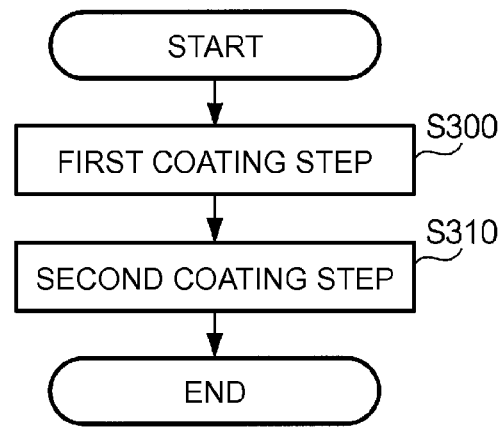
FIG. 7 is a flowchart showing coating steps.

FIG. 7 is a flowchart showing the coating steps of the gas cell array 10 shown as step S100. At step S300 (first coating step), the surface of the grass plate 2 for formation of the gas cell array 10 is coated using OTS molecules. The OTS molecules are an example of first molecules related to the invention.

Figures 8A, 8B, 8C:
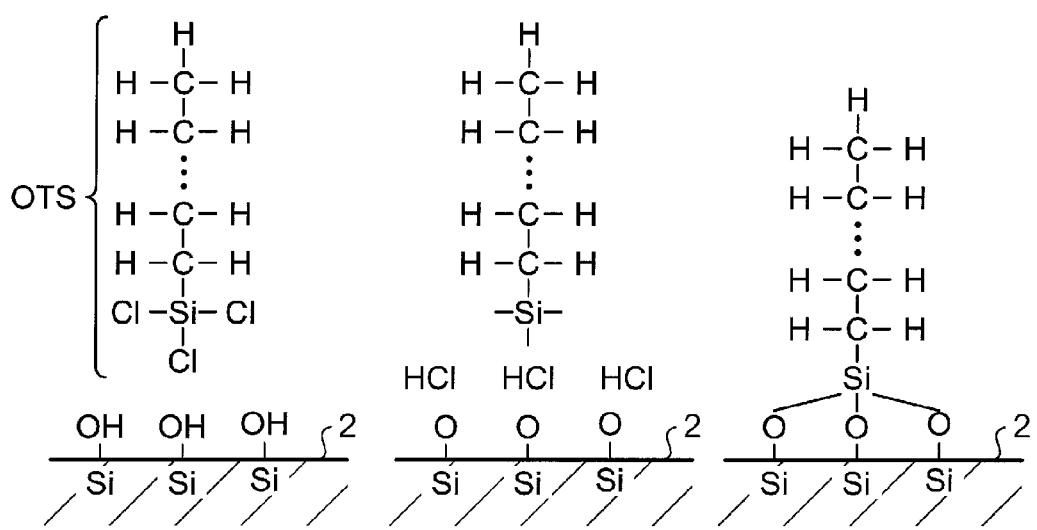
FIGS. 8A to 8C are diagrams for explanation of a process in which an OTS molecule adsorbs to a surface of a glass plate.

FIGS. 8A to 8C are diagrams for explanation of a process in which the OTS molecule adsorbs to the surface of the glass plate 2. As described above, the glass plate 2 is formed using a material such as quartz glass or borosilicate glass. These materials consist primarily of silicon and oxygen, and hydroxyl groups are bonded to the silicon on the surface thereof (see FIG. 8A).

The OTS molecules have functional groups to be chemically bonded to the hydroxyl groups of the glass plate 2 and non-polar groups. The OTS molecules are applied to the surface of the glass plate 2 in a condition in which they are dispersed in a solvent of cyclohexane, hexane, chloroform, or the like. The OTS molecules are applied to both front and rear surfaces of the glass plate 2. When the OTS molecule reaches the hydroxyl group of the glass plate 2, chlorine of the OTS molecule and hydrogen of the hydroxyl group are detached (see FIG. 8B), and the silicon of the OTS molecule and the hydrogen of the glass plate 2 are bonded (see FIG. 8C). By the bonding, the first coating layer is formed by the OTS molecules.

Figure 9:
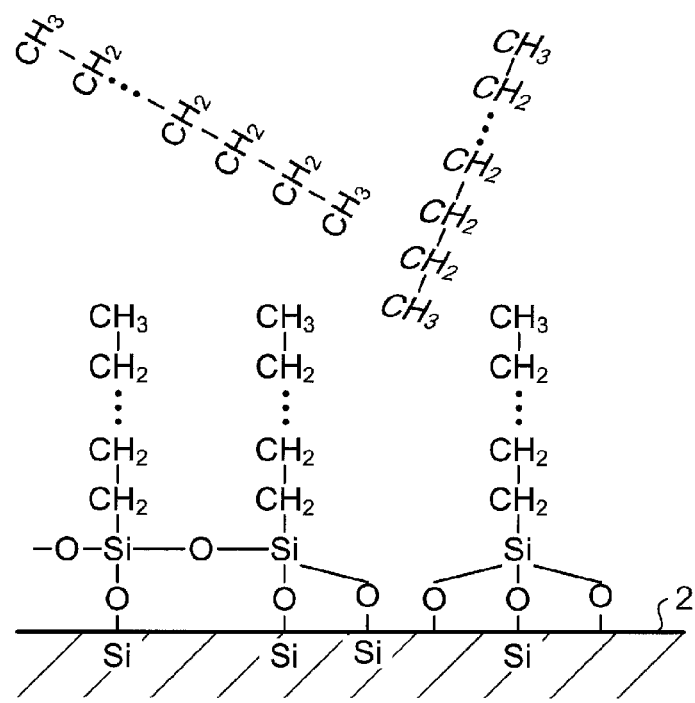
FIG. 9 is a diagram for explanation of bonding of silicon of the OTS molecule and oxygen of the glass plate.

FIG. 9 is a diagram showing another bonding form of silicon of the OTS molecule and oxygen of the glass plate 2. The form of bonding between silicon and oxygen on the surface of the glass plate 2 varies in the respective OTS molecules, not limited to that shown in FIG. 8C. As shown in FIG. 9, oxygen on the surface of the glass plate 2 may be detached from silicon, and two silicon atoms of the OTS molecules and the detached oxygen may be bonded.

Here, reference to FIG. 7 is made again. After the first coating layer is formed by the OTS molecules, at step S310 (second coating step), paraffin molecules are vapor-deposited on the surface of the OTS layer (first coating layer), and a paraffin layer (second coating layer) is formed. The paraffin layer is applied by a dry process or wet process. The paraffin molecules are also applied to both the front and rear surfaces of the glass plate 2 like the OTS molecules.

Figure 10:
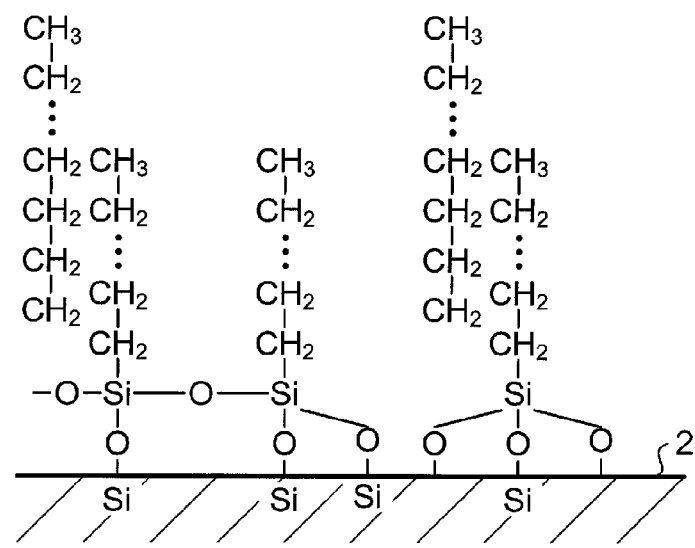
FIG. 10 shows a state in which the paraffin molecules physically adsorb to the OTS molecules.

FIG. 10 shows a state in which the paraffin molecules physically adsorb to the OTS molecules. The paraffin molecules are non-polar molecules, however, strong attractive forces act between the non-polar groups of the OTS molecules and themselves because they have larger molecular weight, and they physically adsorb by the attractive forces. Further, the paraffin molecules can be deposited over the plural layers by the action of the intermolecular attractive forces, and the thickness of the layers can be adjusted.

Figure 11:
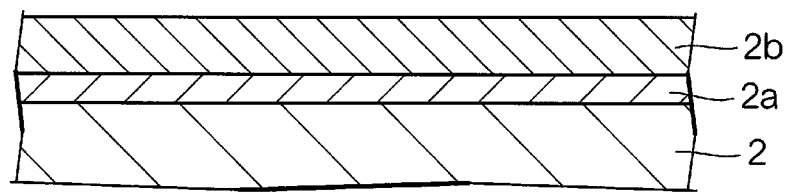
FIG. 11 is a sectional view of the coated glass plate.

FIG. 11 is a sectional view of the coated glass plate 2. At the first coating step, the first coating layer 2a is formed on the surface of the glass plate 2, and the second coating layer 2b is further formed thereon at the second coating step. If these coating layers are adjustable to appropriate thicknesses, the exposure of the polar groups on the surface of the glass plate 2 is reduced and the improvement of the anti-relaxation performance of the spin polarization is expected.

Here, reference to FIG. 6 is made again. At step S110 (cutting step), the glass plate 2 on which the coating layers have been formed is cut.

Figure 12:
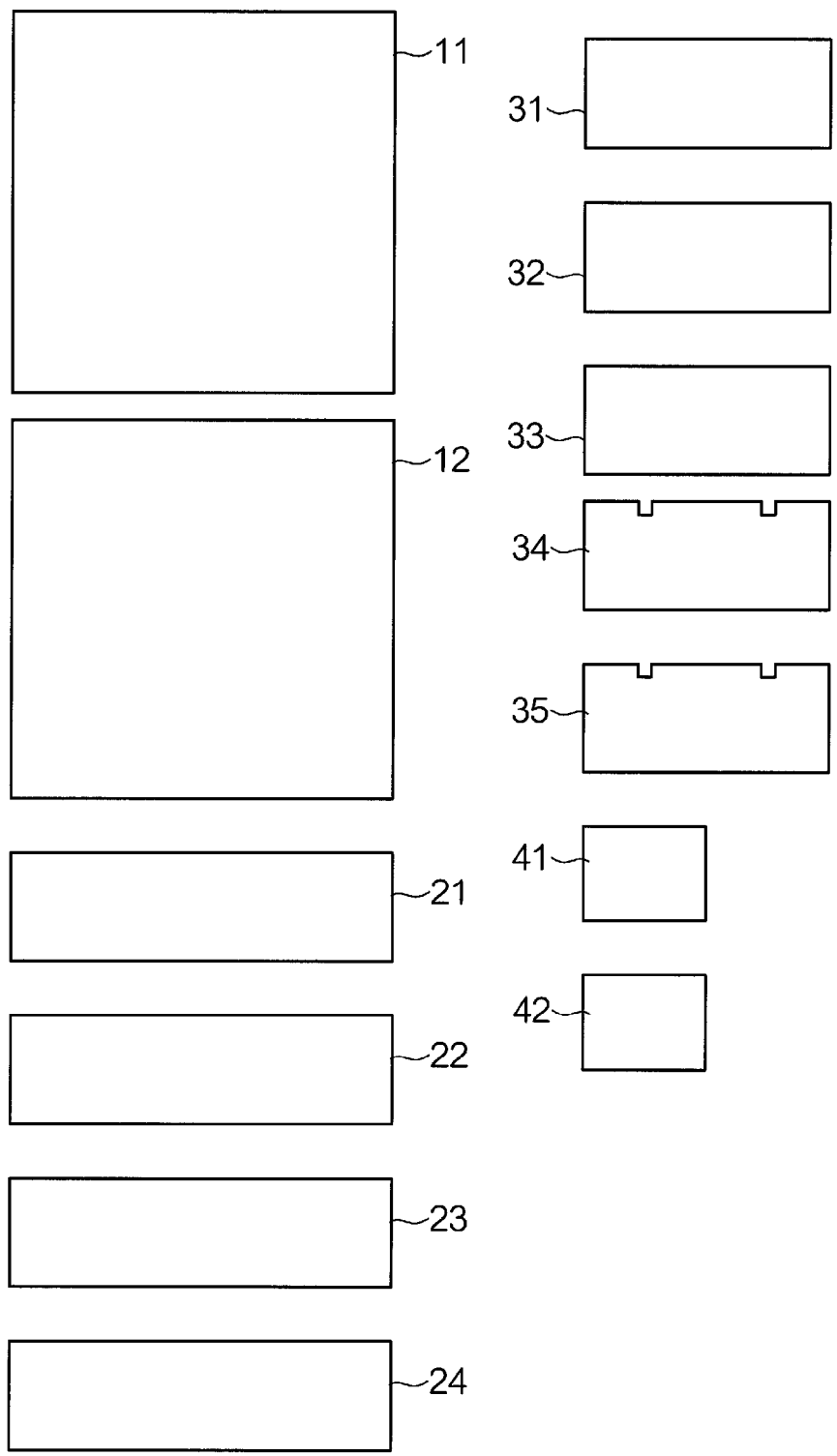
FIG. 12 is a view showing the cut glass plates.

FIG. 12 shows the cut glass plate. A glass plate 11 and a glass plate 12 are members forming the upper surface and the lower surface of the gas cell array 10. Here, "up" refers to the positive z-axis direction and "down" refers to the negative z-axis direction in FIG. 2. A glass plate 21, a glass plate 22, a glass plate 23, and a glass plate 24 are members forming outer side surfaces of the gas cell array 10. "Outer side surfaces" refer to surfaces perpendicular to the xy plane and exposed to the outside. A glass plate 31, a glass plate 32, a glass plate 33, a glass plate 34, a glass plate 35, a glass plate 41, and a glass plate 42 are members forming the gas cells. In the glass plate 34 and the glass plate 35, grooves (concave parts) to be the through holes (through hole 111, through hole 121, through hole 141, and through hole 151) are provided. In this example, the glass plate 31, the glass plate 32, and the glass plate 33 form wall surfaces in parallel to the xz plane. The glass plate 31, the glass plate 32, and the glass plate 33 are arranged in a direction in which the y-axis coordinate becomes larger in this order. The glass plate 34, the glass plate 35, the glass plate 41, and the glass plate 42 form wall surfaces in parallel to the yz plane.

Here, reference to FIG. 6 is made again. At step S120 (assembly step), the cut glass plates are assembled. At this time, they are assembled with at least one surface open for holding an ampule at the next step. For example, all members except the glass plate 11 forming the upper surface of the gas cell array 10 are assembled. In the assembly, the glass plates are joined by welding or bonding using an adhesive agent, for example.

At step S130 (ampule holding step), an ampule is held in the dummy cell 130 within the gas cell array 10. The ampule is put from the open surface.

Figure 13:
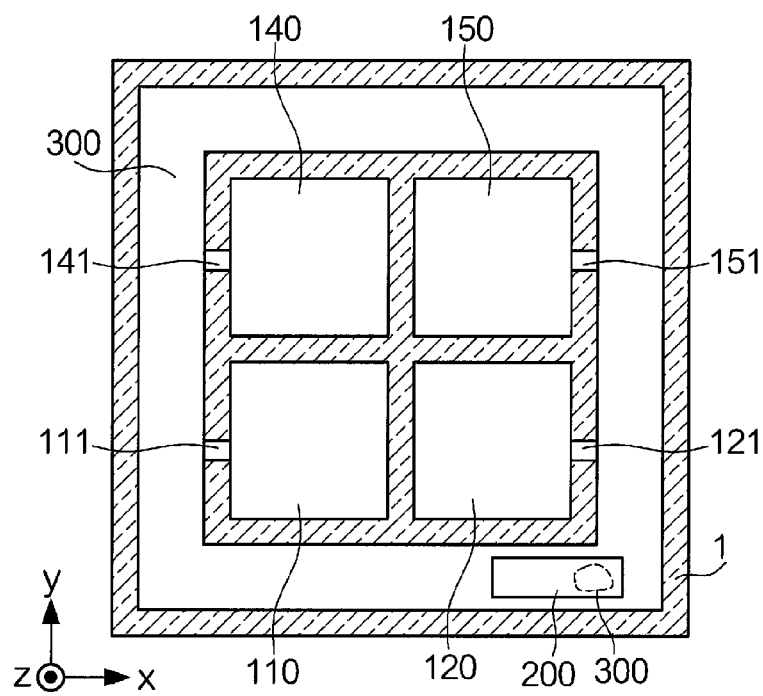
FIG. 13 is a schematic view showing the gas cell array in which an ampule is held.

FIG. 13 is a schematic view showing the gas cell array 10 in which the ampule is held. FIG. 13 shows the same section as that in FIG. 5. Within the ampule 200, an alkali metal solid 300 is enclosed.

Here, reference to FIG. 6 is made again. At step S140 (sealing step), the gas cell array 10 is sealed. In this example, in addition to an alkali metal gas, an inert gas (buffer gas) such as a rare gas is enclosed within the gas cell according to need. In this case, the sealing of the gas cell array 10 is performed in an inert gas atmosphere. Specifically, in the inert gas atmosphere, the member of the open surface (for example, the glass plate 11 forming the upper surface) is joined.

At step S150 (ampule breaking step), the ampule 200 is broken. Specifically, a laser beam focused on the ampule 200 is applied to the ampule 200, and a hole is pierced in the ampule.

At step S160 (gasifying step), the alkali metal solid within the ampule 200 is gasified. Specifically, the alkali metal solid is heated by heating the gas cell array 10, and gasified.

At step S170 (diffusing step), the alkali metal gas is diffused. Specifically, the gas is held at a certain temperature (a temperature higher than the room temperature is desirable) in a fixed period, and thereby, the alkali metal gas is diffused.

Figure 14:
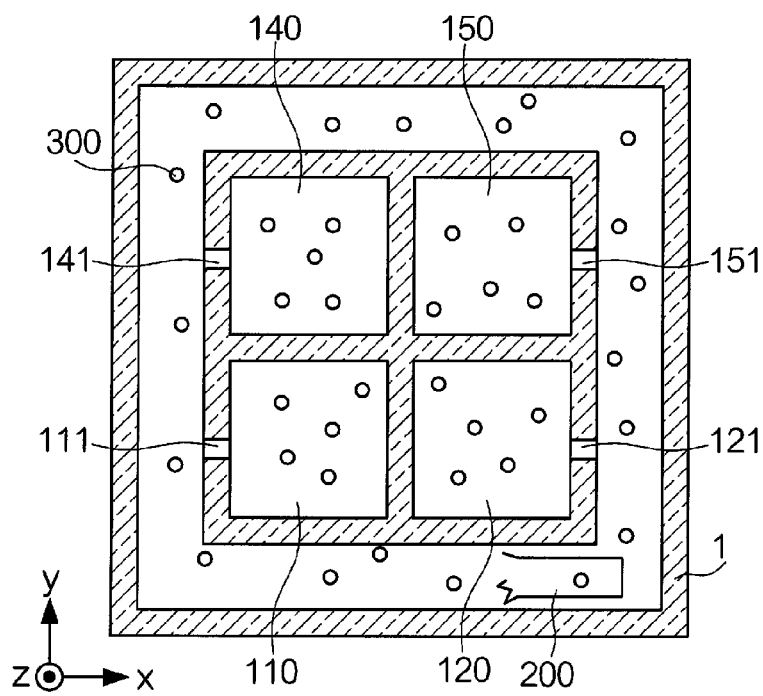
FIG. 14 is a schematic view showing the gas cell array in which alkali metal gas is diffused.

FIG. 14 is a schematic view showing the gas cell array 10 in which the alkali metal gas is diffused. FIG. 14 shows the same section as that in FIG. 5. In FIG. 14, white circles schematically show atoms of the alkali metal gas. At the diffusing step, the alkali metal gas is diffused from the dummy cell 130 into the gas cell 110, the gas cell 120, the gas cell 140, and the gas cell 150 through the through hole 111, the through hole 121, the through hole 141, and the through hole 151. If the time for the diffusing step is taken enough, the alkali metal gas is diffused in all gas cells nearly uniformly.

Note that, in the case where the coating layer is formed by the OTS molecules only, the heat resistance is better, but the number of collisions until the spin polarization disappears is about 2,100 at most and lower than that of paraffin. It is conceivable that this is because shielding in the alkyl groups forming OTS is insufficient and exposure of the polar parts starting from the glass surface and the oxygen atoms of the OTS molecules, paramagnetic impurities such as oxygen, carbon dioxide, or the like increases the adsorption energy of the alkali metal atoms. On the other hand, in the embodiment, the OTS layer is formed on the inner walls of the gas cell and the exposure of the polar groups on the inner wall surfaces of the gas cell may be reduced, and the paraffin layer is formed on the OTS layer and the anti-relaxation characteristics of the inner walls of the gas cell may be improved.

3. Other Embodiments

The invention is not limited to the above described embodiment, but various modifications can be made. As below, several modified examples will be explained. Two or more of the following modified examples may be combined for use.

3-1. Modified Example 1

In the above described embodiment, OTS has been used as the first molecules having functional groups to be chemically bonded to the polar groups of the inner walls of the gas cells and non-polar groups, however, the carbon number of its alkyl group is not limited to that. The first molecules may be another silane coupling agent such as dichlorodimethylsilane, dichlorooctadecylsiloxane, or methyltrichlorosilane. Further, the first molecules may be molecules that express the so-called anchor effect, not limited to the silane coupling agent.

Furthermore, in the above described embodiment, the paraffin has been used as the non-polar second molecule, however, the second molecules are not limited to paraffin. For example, another hydrocarbon may be used. The second molecules may be any non-polar second molecules.

In addition, in the above described embodiment, the gas cell (gas cell array) formed using the material such as quartz glass or borosilicate glass has been used, however, the material forming the gas cell is not limited to the quartz glass or borosilicate glass. Any gas cell including inner walls formed using a compound having polar groups or a material containing the compound may be used.

3-2. Modified Example 2

Figure 15:
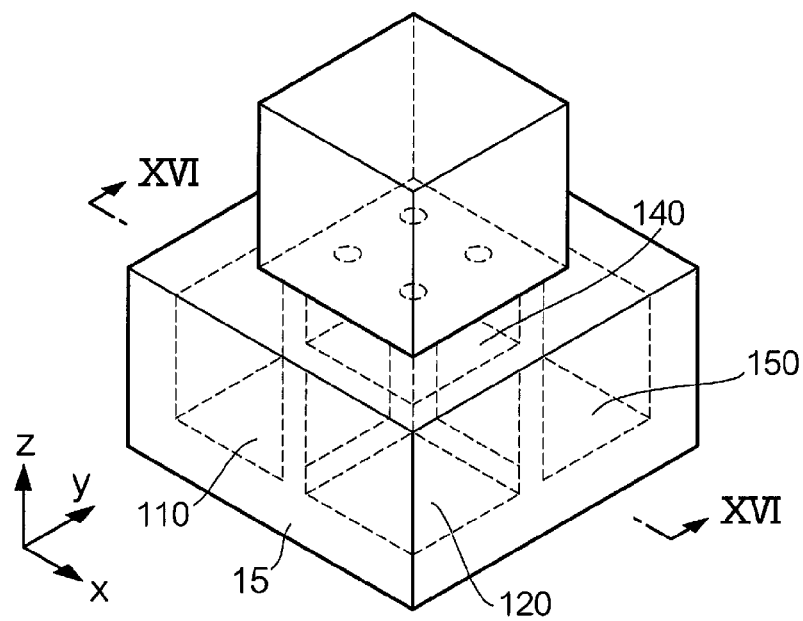
FIG. 15 is an appearance view of a gas cell array according to modified example 2.
Figure 16:
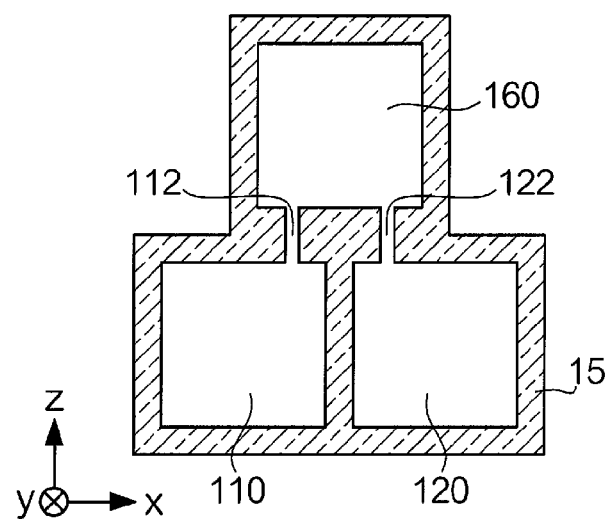
FIG. 16 is a sectional view of the gas cell array along XVI-XVI.

FIG. 15 is an appearance view of a gas cell array 15 according to modified example 2. FIG. 16 is a sectional view of the gas cell array 15 along XVI-XVI. The shape of the gas cell array is not limited to that explained in the embodiment. The gas cell array 15 has a dummy cell 160 in place of the dummy cell 130. The dummy cell 160 is different from the dummy cell 130 of the gas cell array 10 in a positional relationship with the group of gas cells. Note that the dummy cell refers to a cell that does not contribute to measurement of the magnetic field, but is for holding an ampule. The gas cell array 15 has a gas cell 110, a gas cell 120, a gas cell 140, and a gas cell 150, and the dummy cell 160. The group of cells including the gas cell 110, the gas cell 120, the gas cell 140, and the gas cell 150 are two-dimensionally arranged (arranged in a matrix form) on the xy plane. With respect to the group of cells, the dummy cell 160 is stacked on the group of cells (in the positive z-axis direction, i.e., the direction perpendicular to the plane to which the group of cells belong). According to the gas cell array 15, compared to the gas cell array 10, its size on the xy plane may be made smaller. Further, when light having a component in parallel to the xy plane enters, the attenuation of the component of the light in parallel to the xy plane is smaller than that in the gas cell array 10 because the light does not pass the dummy cell.

As shown in FIG. 16, in this example, the gas cell 110 and the gas cell 120 have a through hole 112 and a through hole 122 connected to the dummy cell 160. Though not shown in the sectional view, the gas cell 140 and the gas cell 150 also have through holes connected to the dummy cell 160.

3-3. Modified Example 3

The specific details of the ampule breaking step are not limited to those explained in the embodiment. The ampule 200 may have a part in which two materials having different coefficients of thermal expansion are bonded. In this case, at the ampule breaking step, the ampule 200 (the entire gas cell array holding it) is heated in place of laser beam application. At heating, heat to a degree of breaking the ampule 200 due to the difference in coefficient of thermal expansion is applied.

Further, the breaking of the ampule is not limited to that by the laser beam application. The ampule may be broken by applying dynamic impact or vibration so that the ampule 200 may collide with the inner wall of an ampule container 53. In another example, heat for generating thermal stress may be applied to the ampule 200, and the ampule 200 may be broken by the thermal stress.

3-4. Modified Example 4

The manufacturing method of the gas cell array is not limited to that exemplified in FIG. 6. Another step may be added to the steps shown in FIG. 6. Or, the order of the steps may be changed or part of the steps may be omitted. For example, the order of the coating step and the cutting step may be exchanged. In this case, the glass plate is first cut and the coating layer is formed after the cutting. In another example, after the formation of the coating layer, a step of peeling a part of the layer may be introduced. In this case, of the glass plates, the coating layer in the joint part to the other glass plate is peeled. Or, of the glass plates, the coating layer on the surface exposed to the outside may be peeled.

In another example, the sealing step may be performed under vacuum. In this case, the gas cell has no inert gas, but only the alkali metal gas inside.

3-5. Modified Example 5

The shape of the dummy cell is not limited to that explained in the embodiment. The dummy cell may have a recess part for holding fragment of the ampule. The recess part is provided in a corner part, for example, for minimizing the effect on the measurement of the magnetic field. The recess part may be formed on the glass plate before assembly, or formed by joining a part to be the recess part to the glass plate with a hole. Further, an adhesive material may be accumulated in the recess part so that the fragment of the ampule may not move at transfer (carriage).

3-6. Modified Example 6

The shape of the gas cell is not limited to that explained in the embodiment. In the embodiment, the example in which the shape of the gas cell is rectangular parallelepiped has been explained, however, the shape of the gas cell may be another polyhedron than the rectangular parallelepiped, or a shape having a curved surface in a part such as a cylinder. For example, the gas cell may have a reservoir (metal reservoir) for accumulating the alkali metal solid when the temperature becomes lower to the temperature or less at which the alkali metal atoms solidify. Note that it is only necessary that the alkali metal is gasified at least at measurement and not necessary that the alkali metal is constantly in the gas state.

3-7. Modified Example 7

Figure 17:
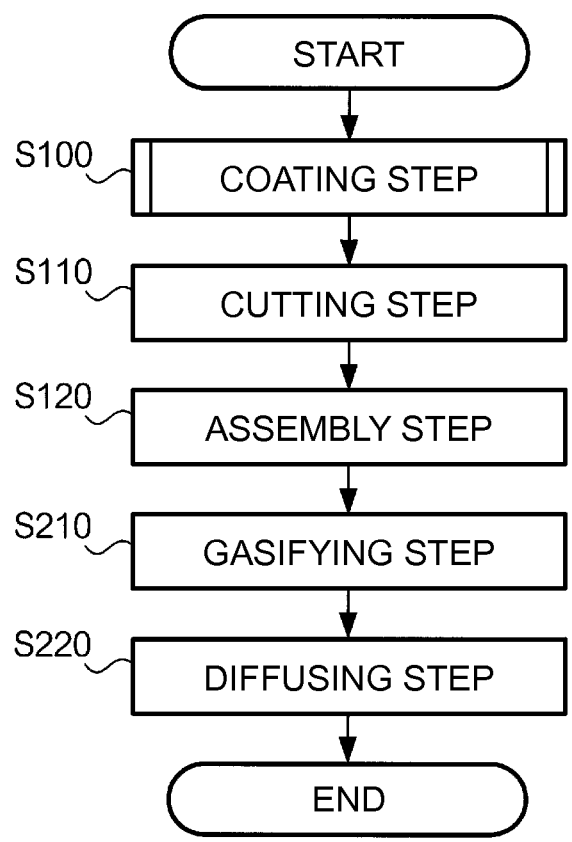
FIG. 17 is a flowchart showing a manufacturing process of a gas cell array according to modified example 7.

FIG. 17 is a flowchart showing a manufacturing process of a gas cell array according to modified example 7. In the flowchart shown in FIG. 17, the processing from step S100 to step S120 is the same as that shown in FIG. 6 in the above described embodiment, and the detailed explanation is omitted here. In this example, the gas cell array has no dummy cell. A part of the gas cell array is connected to a reservoir through a glass tube. In the reservoir, a solid of alkali metal compound is put. At step S210 (gasifying step), the reservoir is heated. The alkali metal compound is decomposed by the heating of the reservoir, and alkali metal gas is generated. At step S220 (diffusing step), the alkali metal gas is diffused in the gas cells via the glass tube. The alkali metal gas that has reached the gas cells is diffused into the respective cells via the through holes. After a sufficient period elapses, the glass tube is heated and cut and the gas cells are sealed. Note that the gas cell array may have a dummy cell.

In yet another example, the manufacturing method of the modified example may be used not for the gas cell array, but for a single gas cell. In this case, no dummy cell is formed, but the alkali metal solid may be directly (without using an ampule) held within the gas cell. Further, the gas cell may be manufactured by glass shaping, or formed by glass processing. In the case of the single gas cell, as is the case of the above described embodiment, the inner walls are coated with the first molecules such as OTS molecules, then further coated with the second molecules such as paraffin thereon, and thereby, the exposure of the polar groups of the inner walls of the gas cell is reduced and the improvement of the anti-relaxation performance of the spin polarization is expected.

3-8. Modified Example 8

In place of the formation of the through holes by laser beam application, a step of generating thermal stress by light application and tearing the ampule 200 by the thermal stress may be used. According to the method, compared to the case where the through holes are formed by light application, degassing (gas emitted from the glass or the like during the step) may be reduced and the sensor characteristics may be improved. In this case, laser having a pulse width of subnanoseconds or less may be used. Further, for facilitation of the tearing of the ampule 200, apart of stress concentration (for example, scratch) may be formed in the ampule 200.

In the above described embodiment and modified examples, the example in which, when the alkali metal atoms are introduced into the gas cells, they are introduced in the solid state has been explained. However, the state when the alkali metal atoms are introduced in the gas cells is not limited to solid. The alkali metal atoms may be introduced into the gas cells in any state of solid, liquid, or gas. Further, a capsule may be used in place of the ampule.

3-9. Modified Example 9

The application of the gas cell is not limited to the magnetic sensor. For example, the gas cell may be used for an atomic oscillator.

The entire disclosure of Japanese Patent Application No. 2012-047700, filed Mar. 5, 2012, is expressly incorporated by reference herein.

What is claimed is:

1. A magnetic measurement system comprising:
   an array of gas cells that are each formed of a material having light transmissivity and being filled with alkali metal gas, the array of gas cells being entirely peripherally surrounded by a dummy gas cell that communicates with each of the gas cells of the array through a hole formed in each gas cell of the array, the through holes of adjacent gas cells of the array being co-axially aligned; and
   a light radiation unit, the light radiation unit configured to irradiate a light onto each of the gas cells of the array,
   wherein each gas cell of the array includes inner glass wall surfaces being coated with a first coating layer and a second coating layer;
   the first coating layer includes methyltrichlorosilane that is chemically bonded to the inner glass wall surfaces of each gas cell of the array; and
   the second coating layer includes non-polar second molecules, which are physically adsorbed to the silane.

2. The magnetic measurement system according to claim 1, wherein the chemical bond between the inner glass wall and the silane is an Si—O—Si bond.

3. The magnetic measurement system according to claim 1, wherein the second molecules are hydrocarbon.

4. The magnetic measurement system according to claim 3, wherein the hydrocarbon is paraffin.

5. A method of fabricating a magnetic measuring system including an array of gas cells and a light radiation unit, the array of gas cells being entirely peripherally surrounded by a dummy gas cell that communicates with each of the gas cells of the array through a hole formed in each gas cell of the array, the through holes of adjacent gas cells of the array being co-axially aligned, and the array of gas cells being formed using a material having light transmissivity and being filled with alkali metal atoms, and inner walls of each of the gas cells of the array being formed of a glass material, the method comprising:
   providing the magnetic measuring system; and
   providing the array of gas cells, the step of providing the array of gas cells including:
      forming a first coating layer by coating the inner glass walls with methyltrichlorosilane material that chemically bonds to silicon atoms in the inner glass walls, and non-polar groups; and
      physically adsorbing a second coating layer having non-polar second molecules to the silane.

6. The magnetic measurement system according to claim 1, wherein the dummy gas cell is unitary with the array of gas cells.

7. The method of claim 5, wherein the dummy gas cell is unitary with the array of gas cells.

* * * * *